United States Patent [19]

Boinot

[11] Patent Number: 4,689,012
[45] Date of Patent: Aug. 25, 1987

[54] DENTAL CONTRA-ANGLE HANDPIECE

[75] Inventor: Jean-Claude Boinot, Roulans, France

[73] Assignee: Micro-Mega S.A., Besancon, France

[21] Appl. No.: 844,454

[22] Filed: Mar. 26, 1986

[30] Foreign Application Priority Data

Apr. 11, 1985 [FR] France .................... 85 06076

[51] Int. Cl.$^4$ .................................. A61C 1/08
[52] U.S. Cl. .................................... 433/126
[58] Field of Search ........................ 433/126

[56] References Cited

U.S. PATENT DOCUMENTS 796,527  8/1905  Patchen ........................ 433/126
3,830,579  8/1974  Roe .............................. 433/126

FOREIGN PATENT DOCUMENTS 0842241  5/1952  Fed. Rep. of Germany ...... 433/127

Primary Examiner—Gene Mancene
Assistant Examiner—Adriene J. Lepiane
Attorney, Agent, or Firm—Robert E. Burns; Emmanuel J. Lobato

[57] ABSTRACT

A dental contra-angle handpiece composed of a front body having a tight fit onto a rear body. The fixing device between the two pieces consists of a key in the form of a segment of a circle which passes through slits cut in the front body, in the rear body and the inner sheath which supports the driving shaft. A ring in the form of a cap which is fitted onto the front body and onto the rear body locks the key. The invention is applicable to all kinds of dental handpieces.

3 Claims, 2 Drawing Figures

DENTAL CONTRA-ANGLE HANDPIECE

FIELD OF INVENTION

The present invention relates to a dental contra-angle handpiece composed of a front body having a tight fit onto a rear body, the front body comprising the contra-angle head in which the tool is fixed and containing an inner sheath which supports the driving shaft of the tool and its bearings, a fixing device being provided for fixing the front body to the rear body, this device comprising a fixing member and a locking ring.

PRIOR ART

Hitherto the front body of the handpiece was generally fixed onto the rear body by means of a circlip mounted between a peripheral groove formed on the outer face of the front body and a peripheral groove formed on the inner face of the rear body, a pin fixed in the front body, which is inserted in a slot in the rear body, ensuring the positioning of the pieces. This device is quite good and has proved itself suitable for a contra-angle handpiece the front portion of which must be able to be easily dismounted and remounted by the dentist with a view to changing the contra-angle head.

Other devices are likewise known for the fixing of the front body of the contra-angle onto the rear body, especially, in accordance with the German Pat. DE 599.591, a ball passes through an orifice in the rear body in order to be introduced into a neck in the front body. This ball is put in place and held by a locking ring which exhibits a cone and which is screwed onto the rear body. This device which may be easily dismounted by the dentist requires in addition a very accurate adjustment in order that the head shall not shift.

Now, not every handpiece must necessarily be able to be dismounted by the dentist, but only by the repairer in the event of breakdown or maintenance, this is why it is not useful to equip certain types of handpiece with an easily dismountable system.

SUMMARY OF THE INVENTION

The present invention is proposed for creating a system which ensures perfect locking between the several pieces and which may be dismantled only by means of a special tool.

For this purpose the handpiece in accordance with the invention is characterized by the fact that the said fixing member consists of a key in the form of a segment of a circle which passes through slits cut in the front body, the rear body and the inner sheath, the said key bearing against the bottoms of the said slits, and that the locking ring forms a cap and is fitted tightly over the front body and the rear body and is equipped at its outer periphery with a groove forming a hold for a tool for dismantling.

Thus there is obtained simultaneously a locking of the front body onto the rear body and of the sheath carrying the shaft into the front body, whereby the pieces can only be dismantled by means of a special tool by a specialist.

BRIEF DESCRIPTION OF THE DRAWINGS

The invention will be described in the description which follows of an embodiment of the handpiece and by means of the attached drawing in which.

DESCRIPTION OF THE PREFERRED EMBODIMENTS

Figure 1:
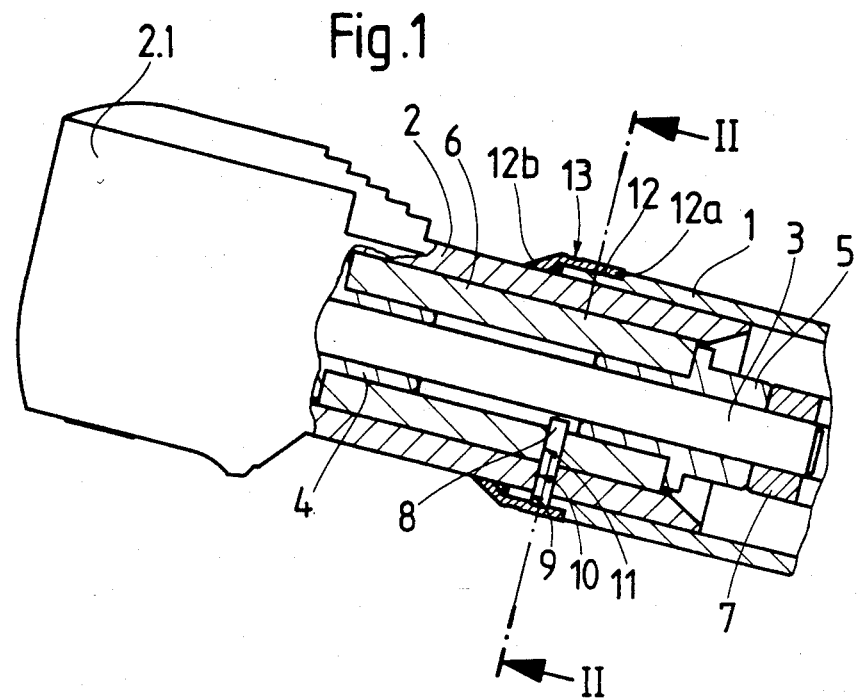
FIG. 1 is a partial longitudinal section of the front portion of the handpiece.
Figure 2:
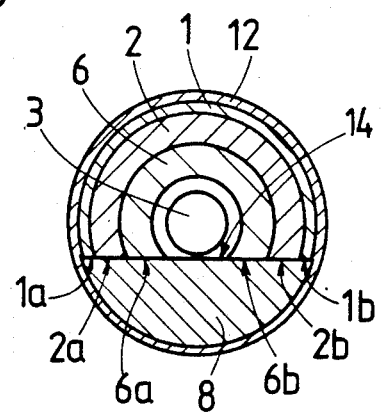
FIG. 2 is a section along the line II—II in FIG. 1.

The handpiece in contra-angle form is composed in known manner of a rear body or sleeve 1 and a front body 2 including the head 2.1 in which is fixed the tool (not shown). The latter is driven in known manner by a rotary shaft 3 supported by bearings 4, 5 which in turn are supported by a sheath 6 fitted tightly into the front body 2. On the rear end of the shaft 3 is mounted a pinion 7 provided for being driven by another pinion mounted on the front end of a second shaft mounted in the rear body and not shown. This second shaft may, for example, be driven by a micromotor housed in a ferrule which is attached to the end of the rear body 1.

The front body 2 is fitted tightly into a socket portion of 1.1 of the rear body 1 and is made integral with the rear body by a key 8 in the form of a segment of a circle which passes through slits 9, 10, 11 cut respectively in the rear body 1, the front body 2 and the inner sheath 6. The key 8 has an accurate peripheral surface with a radius equal to the radius of the external surface of the socket portion 1.1 of the rear body 1 and a plane face 14 forming a chord connecting the ends of the arcurate surface. The plane face 14 of this key, the diameter of which corresponds with the outer diameter of the rear body, bears against the bottom of these grooves or against the faces 1a, 1b of the groove 9 cut in the rear body 1, the faces 2a, 2b of the groove 10 cut in the front body 2 and the faces 6a, 6b of the groove 11 cut in the inner sheath 6. Hence this key 8 at the same time locks the front body 2 onto the rear body 1 and the inner sheath 6 into the rear body 1.

The key 8 is locked on the outside by a ring 12 in the form of a cap the wider rear portion 12a of which is fitted tightly onto the rear body 1, whilst the smaller front end 12b is fitted tightly onto the front body 2. The ring 12 is equipped on its outer face with an annular groove 13 forming a hold for a tool for dismantling, for example, two shells which are engaged in this groove in order to have a hold for pulling this ring 12 towards the head 2.1. This dismantling is in general practised only by the repairer.

This key fixing device may, of course, be applied to all kinds of dental handpieces which do not have to be easily dismountable by the dentist.

What is claimed is:

1. A dental contra-angle handpiece composed of a front body comprising a cylindrical rear portion, a contra-angle head in which a tool is fixed, an inner sheath and a driving shaft rotatably supported in said sheath, and a rear body portion having a socket portion in which said cylindrical rear portion of said front body is snugly received and means for locking said rear body, front body and sheath together, said locking means comprising a flat key having the form of a segment of a circle defined by an arc having a radius equal to the radius of an external surface of said socket portions of said rear body and a chord connecting ends of said arc received in a slot of the same shape in said socket portion of said rear body, said cylindrical area portion of said front body and said sheath and a locking ring fitting tightly on said socket portion of said rear body and engaging said key to hold said key in said slot.

2. A dental contra-angle according to claim 1, in which said locking ring has a forward portion of smaller internal diameter fitting tightly on said cylindrical rear portion of said front body and a rearward portion of larger internal diameter fitting tightly on said socket portion of said rear body.

3. A dental contra-angle according to claim 1, in which said locking ring has in its outer periphery a peripheral groove for receiving a tool for moving said locking ring axially to disengage it from said key.

* * * * *